United States Patent [19]

Kesling

[11] Patent Number: 5,263,859
[45] Date of Patent: Nov. 23, 1993

[54] RELATIVELY FLEXIBLE BONDING PAD FOR AN ORTHODONTIC CERAMIC BRACKET

[75] Inventor: Andrew C. Kesling, LaPorte, Ind.

[73] Assignee: TP Orthodontics, Inc., Westville, Ind.

[21] Appl. No.: 880,898

[22] Filed: May 8, 1992

[51] Int. Cl.$^5$ .............................................. A61C 3/00
[52] U.S. Cl. ................................... 433/9; 433/24
[58] Field of Search ............................ 433/8, 9, 24

[56] References Cited

U.S. PATENT DOCUMENTS

| | | | |
|---|---|---|---|
| 3,250,003 | 5/1966 | Collito | 433/9 |
| 3,765,091 | 10/1973 | Northcutt | 433/9 |
| 3,835,538 | 9/1974 | Northcutt | 433/9 |
| 3,932,940 | 1/1976 | Andren | 433/9 |
| 4,639,218 | 1/1987 | Jones et al. | 433/8 |
| 4,902,224 | 2/1990 | Collins et al. | 433/8 |
| 5,098,288 | 3/1992 | Kesling | 433/9 |
| 5,110,290 | 5/1992 | Wong | 433/5 |

FOREIGN PATENT DOCUMENTS 2741550 3/1979 Fed. Rep. of Germany .......... 433/9

OTHER PUBLICATIONS

Journal of clinical Orthodontics, vol. XXIV, No. 2, Feb. 1990, "Debonding Ceramic Brackets", Elliot R. Storm, D.D.S.

American Journal of Orthodontics and Dentofacial Orthopedics, vol. 97, No. 2, Feb., 1990, "Ceramic Bracket Bonding: A Comparison of Bond Strength With Polyacrylic Acid and Phosphoric Acid Enamel Conditioning", A. J. Maskeroni, D.D.S., et al.

*Primary Examiner*—Cary E. O'Connor
*Attorney, Agent, or Firm*—Lloyd L. Zickert

[57] ABSTRACT

An improved relatively flexible bonding pad or base for an orthodontic ceramic bracket to facilitate debonding the bracket from a tooth and a method of debonding wherein the base or pad is secured to the bracket and the combination bracket and base or pad is bonded to a surface of a tooth. The base or pad is of a relatively flexible material and is formed so that it can be engaged by a pliers for the application of a compressive or buckling force to cause the base or pad to buckle or distort and break the bond to the tooth without the application of any force to the bracket that might cause fracturing of the bracket. The base or pad is provided with one or more holes to enhance the bond between the bracket/pad and the tooth. Following the attachment of the flexible base or pad to a bracket and adhesively bonding the bracket and pad to the tooth, the method of debonding includes application of a compressive edge-to-edge force to the pad that would cause buckling and breaking of the bond with the tooth.

27 Claims, 2 Drawing Sheets

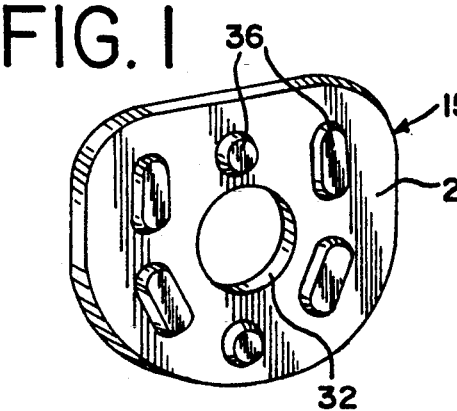
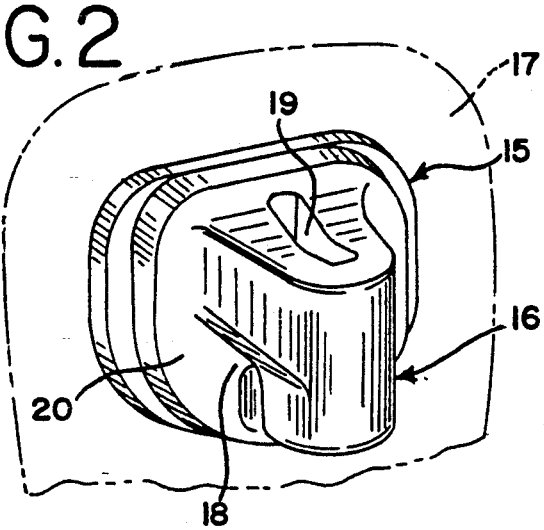
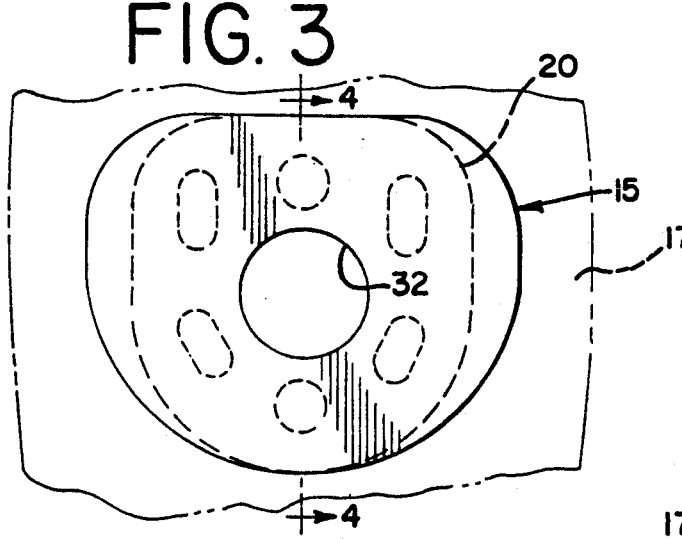
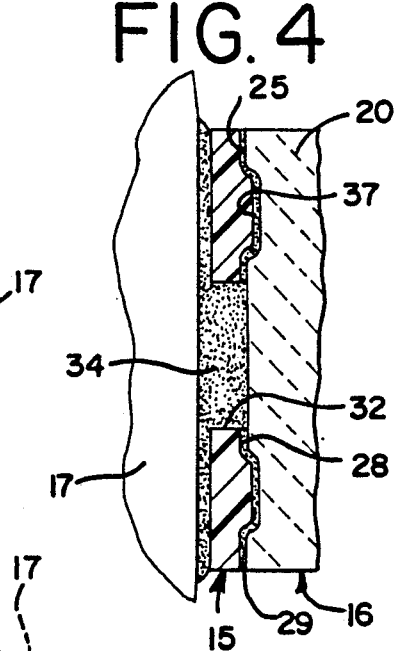
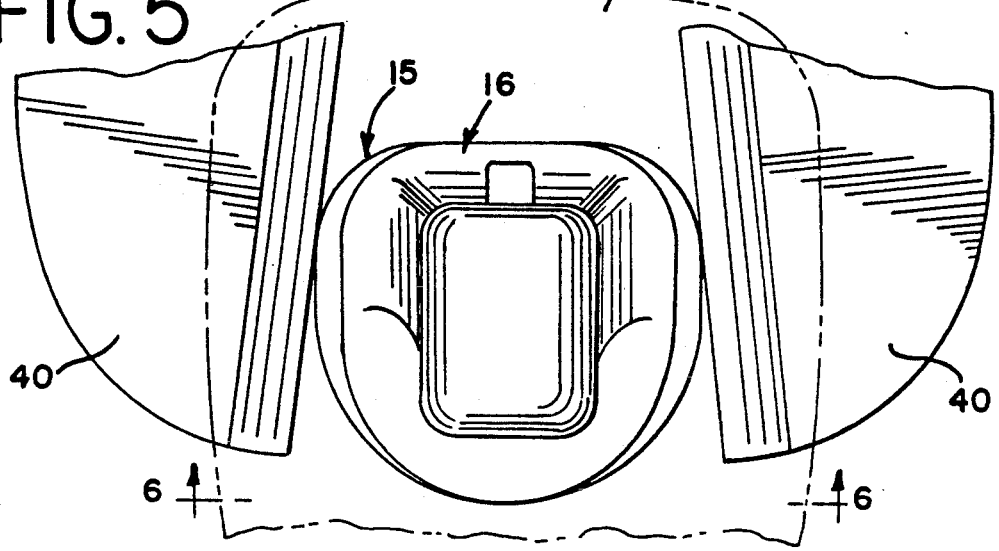

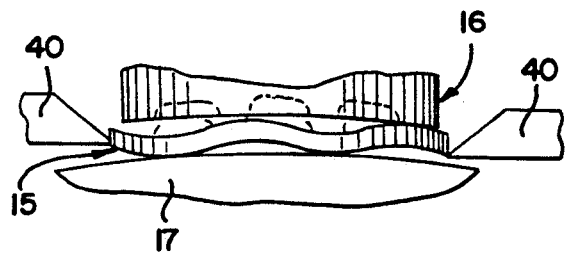
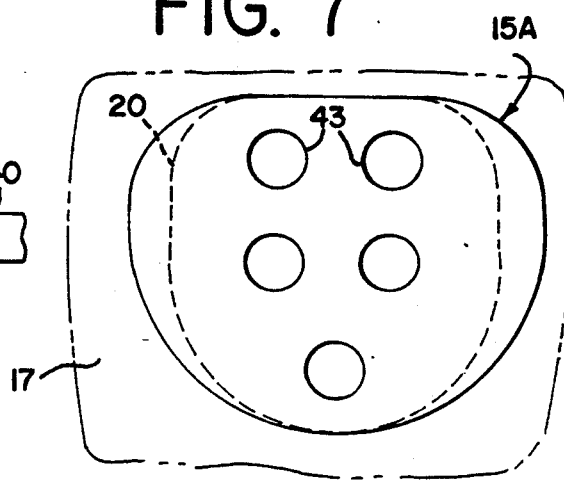
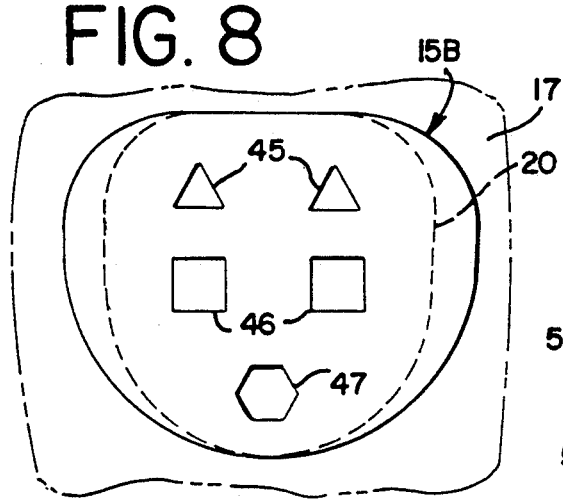
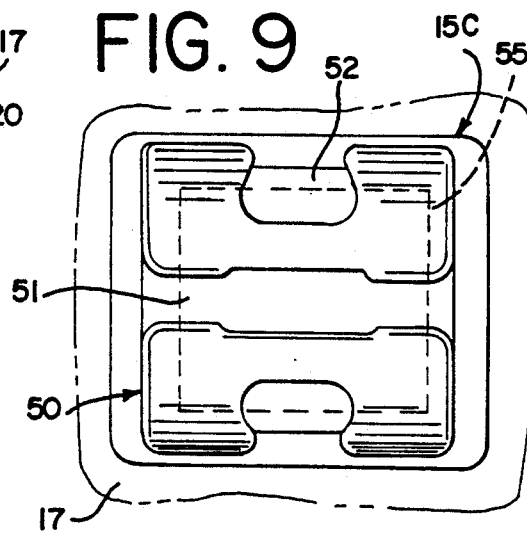
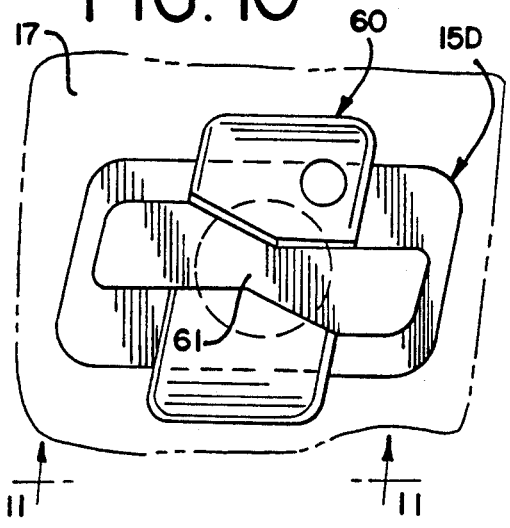
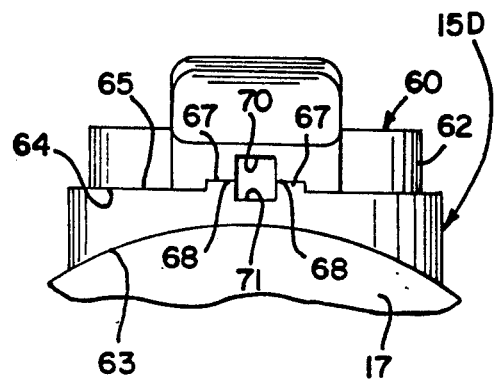

RELATIVELY FLEXIBLE BONDING PAD FOR AN ORTHODONTIC CERAMIC BRACKET

This invention relates in general to an improved flexible pad or base for use with ceramic orthodontic brackets to provide a satisfactory bond while permitting debonding without damaging the bracket or the tooth enamel, and more particularly to a flexible plastic or metal pad or base for a ceramic bracket having a hole through which the bonding adhesive can directly attach to the bracket and wherein the pad or base is sized to be engaged by a pliers during a debonding procedure, and further to a method of bonding a ceramic bracket to a tooth so that it may be easily debonded.

BACKGROUND OF THE INVENTION

Prior to the advent of ceramic brackets, it has been known to provide metal brackets with bonding pads for direct bonding the brackets to teeth. The bonding pads are also of metal and are suitably secured to the brackets. Removal has been accomplished by the use of a standard dental pliers and can be accomplished with respect to all of the brackets in a matter of minutes.

Ceramic brackets made of monocrystalline or polycrystalline material have posed a different problem when they are bonded to teeth, as it is difficult to debond the brackets following their use.

Bonding materials of various types have been used, some of which have greater bonding strength than others. These bonding materials are made and sold by a number of orthodontic supply companies. Ceramic brackets have their bases integrally formed. Such ceramic brackets are often molded and/or machined to final shape. It is a well known problem that removal of bonded ceramic brackets has proved quite difficult and can be very hazardous. For example, when a rigid bracket is removed directly from a tooth, it may cause the bracket to fracture, leaving a part of the bracket on the tooth. The other part of the bracket might shatter in the patient's mouth, setting up a situation where pieces of the bracket which are like glass might be ingested, inhaled or might otherwise damage the tissues of the mouth.

When a part of the ceramic bracket is left on the tooth, it often requires grinding to be removed, and damage can easily be done to the tooth enamel.

Also, it has been known to remove part or all of the enamel during the removal of ceramic brackets, which then is injurious to the health of the tooth. Whenever enamel is removed or the patient injured by the removal of a ceramic bracket, a potential liability problem is created for the orthodontist.

Unlike the time needed to remove metal brackets, the time needed to remove ceramic brackets is substantially greater, which then not only requires more time of the orthodontist but makes the chair time of the patient more uncomfortable.

Ceramic brackets are known to be much more rigid than metal brackets which can somewhat flex or bend during removal. Because of the inability of ceramic brackets to flex, it can be appreciated that greater forces usually are required to remove the bracket during debonding. Whenever the bracket to adhesive interface between a ceramic bracket and the tooth enamel is too strong, there is a high potential for damage of the enamel during debonding. Several attempts have been made to solve the debonding problem associated with ceramic brackets. For example, it is proposed in U.S. Pat. No. 4,455,138 that heat to the dental bracket will assist in loosening the adhesive bonding of the bracket to the tooth so that the bracket may be more easily removed with less forces. However, it has been found that this system was not always practical as the orthodontist may prematurely pull the bracket in anticipation of the loosening of adhesive, causing great pain to the patient and also shattering of the bracket before the heat applied would loosen the adhesive. Further, the pulling force could not be directionally controlled with this system.

Another debracketing tool and method of removal is disclosed in U.S. Pat. No. 4,907,965, where the heat and debracketing force is simultaneously applied. This system does not always assure that the adhesive is sufficiently loose to allow easy removal, and likewise requires engagement of the ceramic bracket during removal.

It is also known to provide a relatively flexible bonding pad or base for an orthodontic bracket to facilitate debonding as disclosed in U.S. Pat. No. 5,098,288. However, it has been found that the bonding between the pad and the bracket often fails during treatment due to the various forces on the bracket during treatment, thereby necessitating rebonding. In such instances, treatment has been interrupted delaying the ultimate conclusion of treatment, and costly chair time is required to rebond the bracket to the tooth.

Further, it has been known to provide a compliant mesh screen of low-density polyethylene between a ceramic bracket and a tooth as disclosed in U.S. Pat. No. 5,110,290. This patent also suggests the compliant layer may be a polyethylene sheet with a plurality of openings.

SUMMARY OF THE INVENTION

The present invention overcomes the heretofore encountered problem in bonding a ceramic bracket having a thin flexible pad or wafer that facilitates debonding from a tooth by providing a pad capable of enhancing the integrity of the bond during the treatment process. The flexible pad or base of the present invention includes a hole or holes therethrough which exposes a part or portion of the base of the bracket to allow the bonding material on the tooth to directly engage and attach to the bracket. This produces a bond having an integrity such that it will withstand the treatment forces encountered in the course of treating a patient. The flexible pad may be plastic or metal having a stiffness along its width or long dimension such that application of compressive forces at opposite edges will cause buckling or distorting of the pad to break the bond with the tooth.

The pad of the present invention thereby functions as a flexible washer between the bracket and the tooth during the time it is bonded to the tooth. During debonding a pliers or debonding tool engages the flexible pad or base to distort or buckle the pad to not only break the bond between the pad and the bracket and/or the tooth but also to cause the bonding material between the tooth and the bracket to shear or fail so that the bracket can be debonded without damaging the bracket or the tooth. This debonding procedure eliminates the need to apply a prying or pulling force directly to the ceramic bracket. The term "buckle" or "buckling" as used herein is intended to mean bending under pressure and resulting in curling or distorting from a normal or usual state.

The pad or base is sized so that it can be engaged and buckled under a force which does not require the direct application of any force to the bracket. Further, the pad or base may be structured to be used for any presently marketed ceramic bracket by being added to the base of the bracket or as part of the bracket structured for mating engagement with a mating surface of the ceramic portion of the bracket. The hole or opening in the pad may take any desired shape. It may be round, oval, square, triangular or any polygonal form, and it may be provided as a single hole or multiple holes. The hole or holes will expose a portion of the base of the bracket that can thereafter be directly bonded to a tooth. The portion of the base exposed may be 30% to 75%, or it may be lower, but the pad must have some contact with the bracket to separate the bracket from the tooth. Further, it may be sized somewhat larger than the bracket base to receive forces from an instrument that will cause the buckling or distorting of the pad to not only break the bond between the pad and the tooth or the pad and the bracket and also to cause the bond directly between the tooth and the bracket to break or fail without requiring the application of any force or forces directly to the bracket.

The flexible pad or base will be of a more flexible material than that of the bracket and the tooth. It is thin and on the order of 0.010 inch thick, and flexible because of being so thin. One satisfactory plastic is a LEXAN resin. LEXAN is a registered trademark of General Electric Company. A satisfactory metal would be stainless steel, and it could be tooth colored.

The method of bonding a ceramic bracket to a tooth according to the present invention includes first coating the entire bracket or at least the base with one or more known silane coupling or bond-enhancement agents to promote adhesion of an adhesive to the bracket because it is known that it is essentially impossible to satisfactorily adhesively connect porcelain or ceramic directly to another surface. Acceptable dental adhesives produce low adhesion between aluminum oxide brackets and teeth and therefore bond-enhancement agents are used. The use of silane coupling agents for ceramic brackets to promote adhesion is well known. These agents are used with both single crystalline and polycrystalline aluminum oxide brackets. One such system of providing a silane coupling agent for a ceramic bracket is disclosed in U.S. Pat. No. 4,948,366. Other silane coupling or bond-enhancement agents are also known for promoting adhesion of ceramic appliances to teeth when using an acceptable dental adhesive.

Following the conditioning of the ceramic bracket with a bond-enhancement coupling agent, a plastic pad or wafer previously conditioned for accepting an adhesive that may be of a polycarbonate resin or an equivalent having a stiffness along its length or long axis and a flexibility along its thickness or short axis such as to allow distortion and buckling under a compressive force along the long axis, is coated with a suitable adhesive. Upon joining of the pad and bracket, the adhesive is cured so that the pad is then suitably attached to the bracket. Alternatively, the pad may be mechanically connected to the bracket, such as by a groove and dovetail connection. Thereafter, using any acceptable dental adhesive and preferably one that is quartz filled such as one of the bonding systems made and sold by TP Orthodontics, Inc. of LaPorte, Ind., the bracket/pad unit may be bonded to a tooth. More specifically, either the self-curing adhesive sold under the registered trademark RIGHT-ON of TP Orthodontics Inc. or the self-curing adhesive sold under the registered trademark 1-TO-1 of TP Orthodontics, Inc. can be used. A satisfactory light-curing adhesive would be of the type sold by TP Orthodontics under the trademark ULTRA LIGHT.

It is therefore an object of the present invention to provide an improved flexible base or pad for an orthodontic bracket to enhance bonding of the bracket to the tooth and thereafter debonding of the bracket from a tooth.

Another object of the present invention is to provide a relatively flexible pad or base of plastic or metal for a ceramic bracket or a bracket that is part ceramic and part plastic to enhance bonding of the bracket to a tooth and to permit debonding without causing the ceramic bracket or ceramic bracket portion to break.

A further object of the present invention is to provide an improved plastic pad or base for a ceramic bracket having at least one hole in the pad so that the bonding adhesive for bonding the bracket and pad to the tooth can directly engage the bracket through the hole, thereby enhancing the strength of the bond between the bracket/pad and the tooth.

Another object of the present invention is in providing an improved plastic or metal pad or base for a ceramic bracket having at least one hole in the pad, thereby exposing the bracket base so that when bonding the bracket pad to a tooth, the bonding adhesive will directly engage the bracket through the opening in the pad, thereby enhancing the strength of the bond between the combination bracket/pad and the tooth while still enhancing debonding, where the pad may be buckled and distorted under the compressive force of an instrument or tool to not only break the bond between the pad and/or the bracket and the tooth but also to cause shearing or failure of the bonding adhesive between the tooth and the bracket.

Another object of the present invention is to provide a method of bonding a ceramic bracket to a tooth which includes applying one or more silane or bond-enhancement coupling agents to the tooth-attaching side of the bracket, adhesively securing a plastic or metal pad to the base of the bracket by applying an adhesive to the pad or bracket and curing that adhesive with the pad in place on the bracket, and utilizing an acceptable dental adhesive for bonding the bracket/pad to a tooth where the dental adhesive will produce a bond directly with the base of the bracket through the opening in the pad.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is a front perspective view of the improved flexible pad of the present invention;

FIG. 2 is a perspective view of a light-wire ceramic bracket mounted on a tooth and having a flexible wafer/pad according to the present invention interposed between the bracket and the tooth;

FIG. 3 is a rear elevation of the bracket and pad unit shown in FIG. 1 illustrating the footprint of the bracket in dotted lines;

FIG. 4 is an enlarged fragmentary transverse sectional view taken substantially along line 4—4 of FIG. 3;

FIG. 5 is a front or labial view of the bracket on a tooth and fragmentarily illustrating the application of jaws or beaks from a pliers for the debonding of the bracket;

FIG. 6 is a partially fragmentary view of a flexible pad under compression from a pliers to illustrate in exaggerated form the breaking of the bond between the pad, the bracket, and the tooth, and also between the tooth and the bracket as seen along line 6—6 of FIG. 5;

FIG. 7 is a modified pad shown in a view similar to FIG. 3 which illustrates the use of a plurality of round holes in place of a single hole;

FIG. 8 is a view similar to FIG. 3 except showing modified openings in the pad to illustrate that the openings may take any desired shape and that they may be polygonal in shape;

FIG. 9 is a front elevational view of an edgewise bracket utilizing a flexible pad according to the present invention showing a rectangular opening in the pad;

FIG. 10 is a front elevational view of another edgewise bracket utilizing the plastic pad of the present invention; and FIG. 11 is an occlusal or bottom plan view of the bracket shown in FIG. 10 and taken generally along lines 11—11 of FIG. 10.

DESCRIPTION OF THE INVENTION

The present invention is in a flexible pad or base for mounting an orthodontic ceramic bracket to a tooth to enhance the bonding and debonding operations. The flexible pad is relatively thin with a thickness on the order of 0.010 inch and may be of plastic or metal. Ceramic brackets are very hard and inflexible. Similarly, teeth are hard and inflexible. Further, the pad of the present invention includes one or more centrally located openings or holes. When adhesively mounting the pad or base on the base of a bracket, a portion of the bracket base will be exposed through the pad to allow the bonding adhesive used to bond the bracket and pad to a tooth. The bonding material extends through the hole and directly bonds with a portion of the base of the bracket. The hole in the pad is sized to define a bond between the bracket and a tooth in addition to the bond between the flexible pad and the tooth such that the bracket and pad will withstand the forces during orthodontic treatment and maintain the integrity of the bond. Essentially, the bond between the bracket and the tooth constitutes the adhesive connection between the bracket and the tooth. While there is an adhesive connection between the pad and the tooth, the strength of the bond is in the adhesive connection between the bracket and the tooth. The hole in the flexible pad may be of any size or geometric shape desired or in the form of a plurality of holes, all being within the footprint of the base of the bracket. The pad is of a material having a stiffness between the opposite edges while being flexible along its width such that a compressive force on opposite edges will cause the pad to buckle and distort to break the bond between the bracket and the tooth.

The flexible pad will be formed to mate with the base of the bracket which may have a curvature compatible with the particular tooth for which the bracket is designed to be used. Further, the flexible pad may be used with ceramic brackets made for the well known Begg light-wire technique or any of the edgewise techniques.

Referring now to the drawings and particularly to the embodiment of FIGS. 1 to 6, the flexible pad of the present invention is generally indicated by the numeral 15 and shown in use for mounting a ceramic Begg or light-wire bracket 16 to a tooth 17. The pad is shaped to cover the bracket base and extend beyond opposite edges of the bracket base. The ceramic material of the bracket may be polycrystalline alumina, monocrystalline alumina, zirconia, glass, or any other suitable ceramic material. The bracket 16 includes a vertically opening archwire slot 18, a pin slot 19, and a base 20. The base 20 of the bracket includes a tooth-attaching face 25 to which the bracket-attaching side 28 of the flexible pad 15 is adhesively secured. While the flexible pad 15 is illustrated in FIG. 4 as being of a plastic material, it will be appreciated that it could be of metal. An adhesive 29 attaches the pad 15 to the tooth.

The pad includes a centrally located hole or opening 32 exposing a portion of the tooth-attaching face of the bracket 16 so that when bonding the bracket/pad unit to the tooth bonding cement will extend through the hole and directly connect with a portion of the base 20 of the bracket, as seen particularly in FIG. 4. The bonding material or cement 34, which will go through the hole in the pad to adhesively connect to the bracket, also adhesively connects the pad to the tooth. That part of the bonding cement that extends through the hole forms a post which interacts with the hole in the pad when interconnecting the bracket to the tooth.

While any suitable type of adhesive may be used to adhesively secure the pad to the bracket, one form of adhesive that is acceptable is a light-curing adhesive which would first be applied to the pad or to the bracket, followed by positioning the bracket on the pad, and then subjecting the adhesive to a light source for curing the adhesive. Any other self-curing adhesive may be used. The combination bracket and pad would be assembled by the manufacturer normally, although the pad could be provided to any user that would in turn mount the pad on a bracket. Prior to adhesively securing the pad to the bracket, both the pad and bracket would be treated with bond-enhancement agents.

The bonding cement or adhesive 34 may be of any suitable type that is available for bonding ceramic brackets to teeth, such as adhesive sold by TP Orthodontics, Inc. of LaPorte, Ind., under the registered trademarks RIGHT-ON and 1-TO-1.

Prior to adhesively securing the pad to the bracket, at least the tooth-attaching surface of the bracket base will be treated with a suitable bond-enhancement or silane coupling agent which facilitates the use of a bonding adhesive to bond the bracket to a tooth. It is well known to prepare ceramic or porcelain brackets with a bond-enhancement agent before applying a bonding adhesive. In a suitable fashion the pad would also be treated for an adhesive. Likewise, the surface of the tooth on which the bracket is to be mounted would also be suitably prepared for enhancing the use of a bonding adhesive.

In order to facilitate the proper orientation of the flexible wafer/pad 15 on the tooth-attaching face of the bracket base 20, a plurality of detents 36 is formed on the bracket-attaching side 28 of the pad to mate with a plurality of indents 37 formed on the tooth-attaching face 25 of the bracket base 20. The detents 36 may be of any suitable geometric shape and would complementarily fit in the mating indents on the bracket. It should be appreciated that the detent/indent orientation elements are optional although they are preferred to facilitate proper orientation of the pad on the bracket. Where the pad is made of plastic, it may be molded or stamped from a sheet; and where it is made of metal, it may be stamped from a sheet and the indents may be suitably formed. While the pad may be initially made with a suitable curvature to mate with a particular bracket base, it will be appreciated that the pad need not be made with a curvature as it can be suitably bent or formed to mate with a curved base when adhesively securing the pad to the base. Further, the pad may have a uniform thickness or be of a varying thickness as shown in the embodiment of FIGS. 10 and 11 and as further explained below.

The flexible pad, whether of plastic or metal, will be of such stiffness along its width between the sides and of such flexibility along its thickness that it will buckle or distort relative to the bracket and the tooth during the debonding procedure when a compressive force is applied between its edges. When made of plastic, the pad may be of a suitable polycarbonate resin or other suitable resin. One such acceptable resin is obtainable from General Electric Company under the registered trademark LEXAN, identified as a 141 or 241 LEXAN resin. Alternatively to being molded, a plastic pad or base could be stamped from a sheet of plastic material.

Preferably, the pad is sized so that it at least extends beyond opposed sides of the bracket base although it may only extend beyond one of the sides of the base. A suitable tool for debonding the bracket would be a suitable cutter in the form of a pliers having opposed movable jaws or beaks 40, as seen in FIGS. 5 and 6. By placing the cutters in position to engage the opposite sides of the pad, as seen in FIGS. 5 and 6, and thereafter applying a suitable compressive force to the pad, the pad will buckle or distort as generally illustrated in FIG. 6, causing the breaking of the bond between the pad and/or the bracket to the tooth, as well as causing the breaking of the bonding material that extends directly between the tooth and the bracket in the hole or opening 32 of the pad without causing damage to the enamel surface of the tooth or the bracket. Thus, the cutting edges of the jaws 40 of the pliers can easily engage the thin flexible pad during the debonding procedure. The compressive force applied to the pad by the pliers is applied along the surface of the tooth 17. It will be appreciated that the use of a cutter, as illustrated in FIGS. 5 and 6, is not intended to be the only type of tool that could be used for applying the necessary compressive force to the pad. Other suitable tools could be used. Use of the pliers is such that it avoids contact with the bracket and the accidental fracturing of the bracket. In the event the bracket would be fractured, it raises a possibility that a part of the bracket may be ingested by the patient which could cause injury to the patient. Application of the compressive force on the pad effectively causes the bracket to pop off the pad and the tooth. Any remaining bonding adhesive on the tooth can thereafter be easily removed by a scaler or suitable deburring tool.

As seen in FIG. 3, the footprint of the bracket base 20 is smaller than that of the pad 15. Further, it will be appreciated that the opening or hole 32 may be sized much larger than that shown in FIG. 3, although it is preferred that the opening is sized within the footprint of the bracket base.

A modified flexible pad 15A is illustrated in FIG. 7 which differs generally from the embodiment of FIGS. 1 to 6 in that a plurality of holes or openings 43 is provided in the pad in place of the single opening 32 in FIG. 1. Like the opening 32, the holes 43 are also round, although it should be appreciated they could be oval or of any other geometric shape.

A further modified flexible pad is shown in FIG. 8 and generally indicated by the numeral 15B, wherein it differs from the embodiments of FIGS. 1 to 6 and FIG. 7 in that the geometric shape of the openings or holes in the pad are polygonal. Pad 15B includes triangular holes 45, square holes 46, and hexagonal holes 47.

A still further pad embodiment is shown in FIG. 9 and formed to be used with an edgewise bracket. The pad in FIG. 9 is generally indicated by the numeral 15C and is generally rectangular in form for use with an edgewise bracket 50 of the type disclosed in U.S. Pat. No. 4,799,882. This bracket generally includes a horizontally opening archwire slot 51 and a base 52. The flexible pad 15C extends beyond the footprint of the base 52 at all sides unlike the pad 15 in the first embodiment which extends only beyond the footprint of the bracket base at two opposite sides. Additionally, the hole in the pad 15C, which is generally indicated by the numeral 55, is rectangular in shape and of a relatively large size to expose about 70% to 75% of the bracket base 52 for being bonded directly to the tooth. Thus, this embodiment illustrates a pad having a relatively large opening for enhancing the bonding of the bracket and pad to a tooth.

Another type of edgewise bracket is illustrated in FIGS. 10 and 11, wherein the pad is generally indicated by the numeral 15D and the bracket is generally indicated by the numeral 60. This bracket is also ceramic and of the form that is disclosed in U.S. Pat. No. 4,842,514. Bracket 60 includes a horizontally opening archwire slot 61 and a base 62, as seen particularly in FIG. 11. The pad 15D is rhomboidal as is the general outline of the front profile of the bracket 60 and formed to have a curved tooth-attaching side 63 for mating with the tooth 17. The thickness of the pad is thinner at the center than at the outer edges, as seen in FIG. 11, so as to accommodate the tooth-facing side 64 of the bracket which is generally flat. Thus, the bracket-attaching side 65 of the pad 15D is also substantially flat. The bracket-attaching side 65 of the pad includes a pair of ribs 67 that mate with recesses 68 formed on the bracket to provide an orientation or alignment mechanism between the bracket and the pad. Additionally, the bracket includes a vertical groove or slot 70 which aligns with a vertical groove or slot 71 of the pad to form a vertical opening for receiving auxiliaries.

The pads of the embodiments of FIGS. 7 to 11 are adhesively secured to the bracket in the same manner as the pad 15 of the first embodiment was described as being secured to the bracket 16. Similarly, the ceramic brackets of FIGS. 9 and 10 are suitably treated with bond-enhancement agents prior to adhesively securing the pad to the bracket. Finally, the bonding adhesive used to attach the bracket and pad combinations of FIGS. 7 to 10 would be of a like type as described above in connection with attaching the bracket pad combination of the embodiment of FIG. 1 to a tooth. Further, it will be appreciated that debonding of the brackets having pads like those in FIGS. 7 to 10 will be accomplished in the same manner as described in connection with the debonding of the pad of bracket 16 in the embodiment of FIGS. 1 to 6. Any geometrical hole or opening may be used in any of the pads illustrated.

Thus, a rectangular, square, triangular, or other polygonal shape may be used in the pad 15 in place of the round hole.

Alternatively, the flexible pad may be mechanically connected to the bracket. Any suitable mechanical connecting arrangement may be provided. For example, a groove and dovetail connection could be employed. In the event a mechanical connection is provided, it would not be necessary to use an adhesive between the bracket and the pad.

In view of the foregoing, it will now be appreciated that the flexible pad of the present invention is an improvement over the flexible pad of U.S. Pat. No. 5,098,288 mentioned above by providing opening means in the pad so that the bonding adhesive for bonding the bracket to a tooth can directly engage and attach to at least a portion of the bracket base. At the same time, the advantages of debonding set forth in the above patent are retained with the present invention in order to prevent damage to tooth enamel or fracture of the bracket.

It will be understood that modifications and variations may be effected without departing from the scope of the novel concepts of the present invention, but it is understood that this application is to be limited only by the scope of the appended claims.

I claim:

1. A flexible base/pad adapted to be connected to a ceramic bracket, said base/pad having a bracket-engaging side and a tooth-engaging side, means for connecting the bracket-engaging side to the bracket, said base/pad having a hole therein which exposes a portion of the bracket and permits bonding material on the tooth to flow into the hole and contact the bracket to bond the bracket and base/pad directly to the tooth in the area defined by said hole, said base/pad being sized relative to the bracket to be easily engageable by a pliers during debonding without the pliers applying any force to the bracket, and said base/pad being of such stiffness along its width and such flexibility along its thickness that application of a squeezing force by the pliers will buckle or distort the base/pad to break the bond between the bracket and the base/pad and/or the base/pad and the tooth and in the area defined by said hole.

2. The base/pad of claim 1, wherein the base/pad is of plastic material.

3. The base/pad of claim 1, wherein the bracket is of metal.

4. The flexible base/pad of claim 1, wherein said pad includes a plurality of holes.

5. The combination of a ceramic orthodontic bracket having a tooth-facing side and a relatively thin and flexible pad, said pad having a bracket-attaching side connected to the tooth-facing side of the bracket, and a tooth-attaching side adapted to be bonded to the surface of a tooth, the tooth-facing side of the bracket and the bracket-attaching side of the pad including means for aligning the pad to the racket when connecting the pad to the bracket, and said pad having a hole therein directly exposing a portion of the tooth-facing side of the bracket which permits bonding material on the tooth to flow into the hole and bond directly to the bracket to bond the bracket/pad to the tooth in the area of the hole, and said base/pad being sized to extend beyond at least two opposed edges of the tooth-engaging side of the bracket to be engageable at the edges by means for application of a compressive force without contacting the bracket and said pad being of such stiffness along its width and such flexibility along its thickness to cause buckling of the pad and breaking of the bond when subjected to a squeezing force at its edges while debonding the bracket from the tooth.

6. The combination of claim 5, wherein the hole is sized to expose about 30% to 75% of the tooth-facing side of the bracket.

7. The combination of claim 5, wherein said aligning means includes indents on one of the tooth-facing side of the bracket or the bracket-attaching side of the pad and detents on the other of the tooth-facing side or the bracket-attaching side.

8. The combination of claim 5, wherein said aligning means includes ribs on one of the tooth-facing side of the bracket or the bracket-attaching side of the pad and recesses matingly receiving the ribs on the other of the tooth-facing side or the bracket-attaching side.

9. The combination of a ceramic orthodontic bracket having a tooth-facing side and a relatively thin and flexible plastic pad of polycarbonate material on the tooth-facing side, said pad having a bracket-attaching side adhesively secured to the tooth-facing side of the bracket, and a tooth-attaching side adapted to be bonded by a bonding material to the surface of a tooth, said pad having at least one hole therethrough to expose a portion of the tooth-facing side of the bracket directly to the tooth and allowing the bonding material to go into the hole and directly bond the tooth to the exposed portion of the tooth-facing side of the bracket to enhance bonding the bracket to the tooth, said pad being sized to extend beyond at least one edge of the tooth-attaching side of the bracket to be engageable by means for application of a compressive force between its edges, and said pad being of such stiffness along its width and such flexibility along its thickness to cause buckling of the pad and breaking of the bond when subjected to a compressive force while debonding the bracket from the tooth.

10. The combination of a ceramic orthodontic bracket having a tooth-facing side and a relatively thin and flexible plastic pad on said tooth-facing side, said pad having a bracket-attaching side, an adhesive over the pad securing the bracket-attaching side of the pad to the tooth-facing side of the bracket, said pad having a tooth-attaching side adapted to contact bonding material for attaching the bracket/pad onto the surface of a tooth, at least one hole in the pad directly exposing a portion of the tooth-facing side of the bracket to the tooth and allowing the bonding material to go through the pad and bondingly engage the exposed portion of the bracket to the tooth in the area of the hole to enhance bonding of the bracket with the tooth, and said pad being sized to extend laterally beyond at least one edge of the tooth-engaging side of the bracket to be engageable by means for application of a compressive force between its edges, and said pad being of such stiffness along its width and such flexibility along its thickness to cause buckling of the pad and breaking of the bond when subjected to a compressive force during debonding the bracket from the tooth.

11. The combination of a ceramic bracket and a flexible pad for the bracket, said bracket including a base to which the pad is secured, said pad having at least one hole therethrough exposing 30% to 75% of the bracket, adhesive securing said pad to the bracket, wherein said hole increases the bonding of the bracket to the tooth when bonding the bracket/pad to a tooth to enhance the bond strength of bracket, and said pad being sized slightly larger than the base to extend laterally beyond at least one edge of the base to be engageable by means for application of a compressive force between its edges, and said pad being of such stiffness along its width and such flexibility along its thickness to cause buckling of the pad and breaking of the bond when subjected to a compressive force while debonding the bracket from the tooth.

12. The combination of claim 11, wherein the hole is round.

13. The combination of claim 11, wherein the hole is oval.

14. The combination of claim 11, wherein the hole is polygonal.

15. The combination of claim 11, wherein the hole is square.

16. The combination of claim 11, wherein the hole is rectangular.

17. The combination of claim 11, wherein the hole is within the periphery of the base.

18. The combination of claim 11, wherein the pad includes a plurality of holes, all of which are within the periphery of the base.

19. The combination of claim 18, wherein the holes are round.

20. The combination of claim 18, wherein the holes are polygonal.

21. A flexible base for a ceramic bracket, wherein the base is adhesively attached to the bracket, said base being thin and on the order of 0.010 inch thick and having a bracket-engaging side adapted to be adhesively bonded to the bracket and a tooth-engaging side adapted to be adhesively bonded to a tooth, said base having a hole centrally disposed therein exposing a portion of the base and permitting bonding material on the tooth to extend through the hole and adhesively attach to the bracket to enhance bonding with the tooth, said base being sized larger than the bracket to be easily engaged by jaws of a pliers so that a compressive force can be applied to opposite edges during debonding the bracket from a tooth, and said base having a stiffness between the edges and a flexibility along its thickness such that application of a sufficient compressive force at opposite edges will cause the base to buckle or distort and break the bond between the base and/or the bracket and tooth and between the base and the bracket.

22. The flexible base of claim 21, wherein the base is plastic.

23. The flexible base of claim 21, wherein the base is metal.

24. A method of bonding a ceramic bracket to a tooth, wherein the bracket has a base with a tooth-attaching surface, the method comprising the steps of applying a silane coupling agent to the tooth-attaching surface of the bracket, securing a plastic pad having a centrally disposed hole therethrough to the tooth-attaching surface of the bracket such that a portion of the tooth-attaching surface is exposed through the hole and the size of the hole is such that it is within the periphery of the tooth-attaching surface, and adhesively securing the bracket/pad to the tooth with a bonding material that substantially fills the hole of the pad and attaches to the silane treated bracket-attaching surface of the bracket.

25. The method of claim 24, wherein the step of securing the pad to the bracket includes application of an adhesive to the surface of the pad that engages the tooth-attaching surface of the bracket, joining the pad to the bracket, and curing the adhesive.

26. The method of claim 25, wherein the adhesive is light-curing and the step of curing includes the application of light to the adhesive.

27. A method of bonding a bracket to a tooth and thereafter debonding the bracket from the tooth, wherein the bracket has a base with a tooth-attaching surface, the method of bonding comprising the steps of applying a silane coupling agent to the tooth-attaching surface of the bracket, adhesively securing a plastic pad having a centrally disposed hole therethrough to the tooth-attaching surface of the bracket such that a portion of the tooth-attaching surface is exposed through the hole and the size of the hole is such that it is within the periphery of the tooth-attaching surface, and adhesively securing the bracket/pad to the tooth with a bonding material that substantially fills the hole of the pad and attaches to the silane treated bracket-attaching surface of the bracket, the method of debonding including the steps of positioning the jaws or beaks of a pliers to the opposing sides of the pad, and applying a compressive force such as to cause the pad to buckle and break the bond between the pad and/or the bracket and tooth and to cause the adhesive between the bracket and the tooth to fail.

* * * * *